United States Patent [19]

Fischer

[11] Plant 5,065

[45] Jul. 5, 1983

[54] AFRICAN VIOLET NAMED PINK LADY

[75] Inventor: Arnold W. Fischer, Hanover, Fed. Rep. of Germany

[73] Assignee: Pan-American Plant Company, Parrish, Fla.

[21] Appl. No.: 252,894

[22] Filed: Apr. 10, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new African Violet cultivar distinguished by its profuse production of large, star-shaped, phlox pink flowers bloomed intermittently and borne upright above the foliage on strong, erect stems on a plant of generally rosette shape characterized by a strong, vigorous and rapid growth habit.

4 Drawing Figures

BACKGROUND OF THE NEW PLANT

This new African Violet cultivar originated as a seedling of unknown parentage grown in a field of African Violet plants maintained by me at Hanover, West Germany, for breeding purposes, this new plant having been discovered by me in 1973 and selected for observation because of its large, star-shaped and phlox pink blooms. This plant was propagated by me by means of cuttings at Hanover and such propagation was carried on through many successive generations in my greenhouse at Hanover, which demonstrated conclusively that the novel characteristics of this plant would hold true from generation to generation and appeared to be firmly fixed. Propagation of this new African Violet plant on a commercial scale is now being done at West Chicago, Ill., and at Parrish, Fla., U.S.A., by means of leaf cuttings.

DESCRIPTION OF THE DRAWINGS

This new violet plant is illustrated by the accompanying drawings, of which sheet 1 is a photographic view of a potted plant in full bloom, sheet 2 is a photographic print showing a full face view of a flower of this variety which has been hand-painted to show the true flower colors, and sheets 3 and 4 are prints of machine copies of the front and back sides, respectively, of typical leaves of this plant.

DESCRIPTION OF THE NEW PLANT

The following is a detailed description of the new plant based upon observations made in greenhouse at West Chicago, Ill., U.S.A., the color designations being according to The R.H.S. Colour Chart published by The Royal Horticultural Society of London, England.

THE PLANT

Origin: Seedling.
Parentage: Unknown.
Classification:
*Botanic.*—*Saintpaulia ionantha.*
*Commercial.*—African Violet.
Form: Compact and rosette shaped.
Growth: Strong and vigorous.
Growth Rate: Rapid.
Foliage:
*Quantity.*—Abundant, with about 17 leaves.

*Size of leaf.*—Length — From insignificant to about 70 mm. Width — From insignificant to about 70 mm.
*Shape.*—Oval with rounded apex and cordate base.
*Margin type.*—Sinuate.
*Texture.*—Pubescent.
*Aspect.*—Glossy.
*Color.*—Upper Side — 137A. Under Side — 138C.
*Ribs and veins.*—Pinnate.
*Petioles.*—Length: Various, from insignificant to about 80 mm.

THE BUD

Form: Globular.
Size: Average with various lengths and diameters.
Opening rate: Typical violet.
Color of petals:
*When sepals divide and petals begin to unfurl-*.—161A.
Sepals:
*Number.*—Five.
*Shape.*—Lanceolate and branched, becoming flat when flowers open.
*Color.*—Inside — 199A. Outside — 199A.
*Striae.*—None.
Calyx:
*Size.*—Small.
*Shape.*—Splits to star-shaped.
*Aspect.*—Hairy.
Peduncle:
*Length.*—Varies from insignificant to about 65 mm.
*Texture.*—Smooth.
*Strength.*—Erect and rigid.
*Color.*—176A.

THE FLOWER

Blooming habit: Intermittent with profuse production of blooms.
Size: Large.
*Diameter.*—About 34 to 53 mm.
Borne: As a cyme.
Shape:
*When bloom first opens.*—Cup-shaped, becoming flat as bloom matures.
Petalage:
*Number of petals.*—Five.
*Arrangement.*—Sympetalous.

*Form.*—Actinomorphic and rotate with obtuse apex and repand margin.

*Texture.*—Soft.

*Appearance.*—Satiny.

*Color.*—Top Side — 62B. Reverse Side — 62D.

Petaloids: None.

Flower stem:

*Length.*—From insignificant to about 65 mm.

*Strength.*—Strong and upright.

*Color.*—176A.

Persistence: Flowers hang on and dry.

Fragrance: None.

Lasting quality: About 10 to 20 days on the plant.

REPRODUCTIVE ORGANS

Stamens:

*Anthers.*—Five in number in monadelphous arrangement. Size: About 3 mm. square. Color: Yellow.

*Filaments.*—Length: About 4 mm. Color: Whitish-yellow.

*Pollen.*—Color — Yellow.

Pistils:

*Number.*—One.

*Style.*—Length: About 7 mm. Color: 62A.

*Stigma.*—Color — Whitish.

Ovaries: Hypogynous and tomentose.

This new variety of African Violet plant is distinguished by its rapid and vigorous growth and its profuse production of blooms borne in a bouquet above the medium green foliage which produces the rosette plant form, and by the large, star-shaped and phlox pink coloration of the flowers which have a good keeping quality.

I claim:

1. A new African Violet cultivar, substantially as herein shown and described, characterized by the large, star-shaped flowers and the phlox pink coloring of its profusely produced flowers.

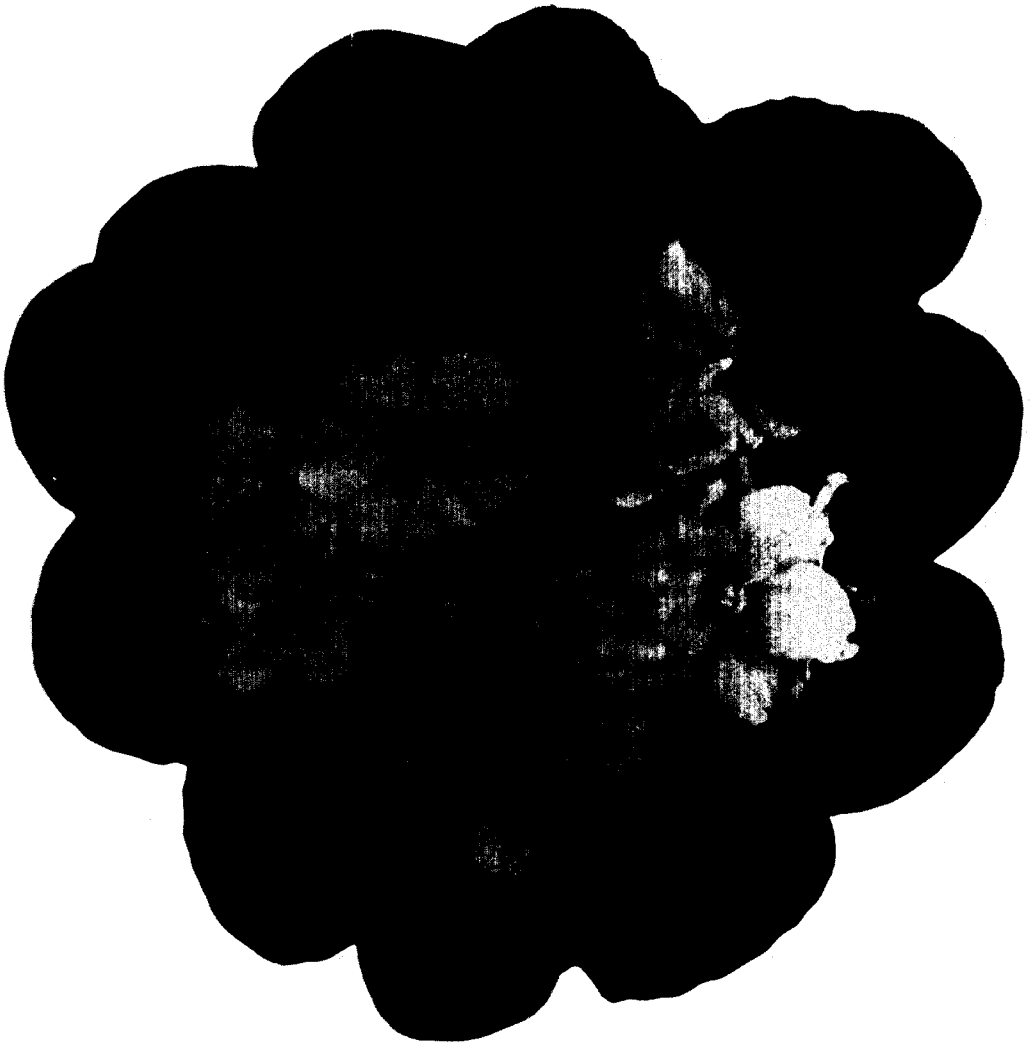

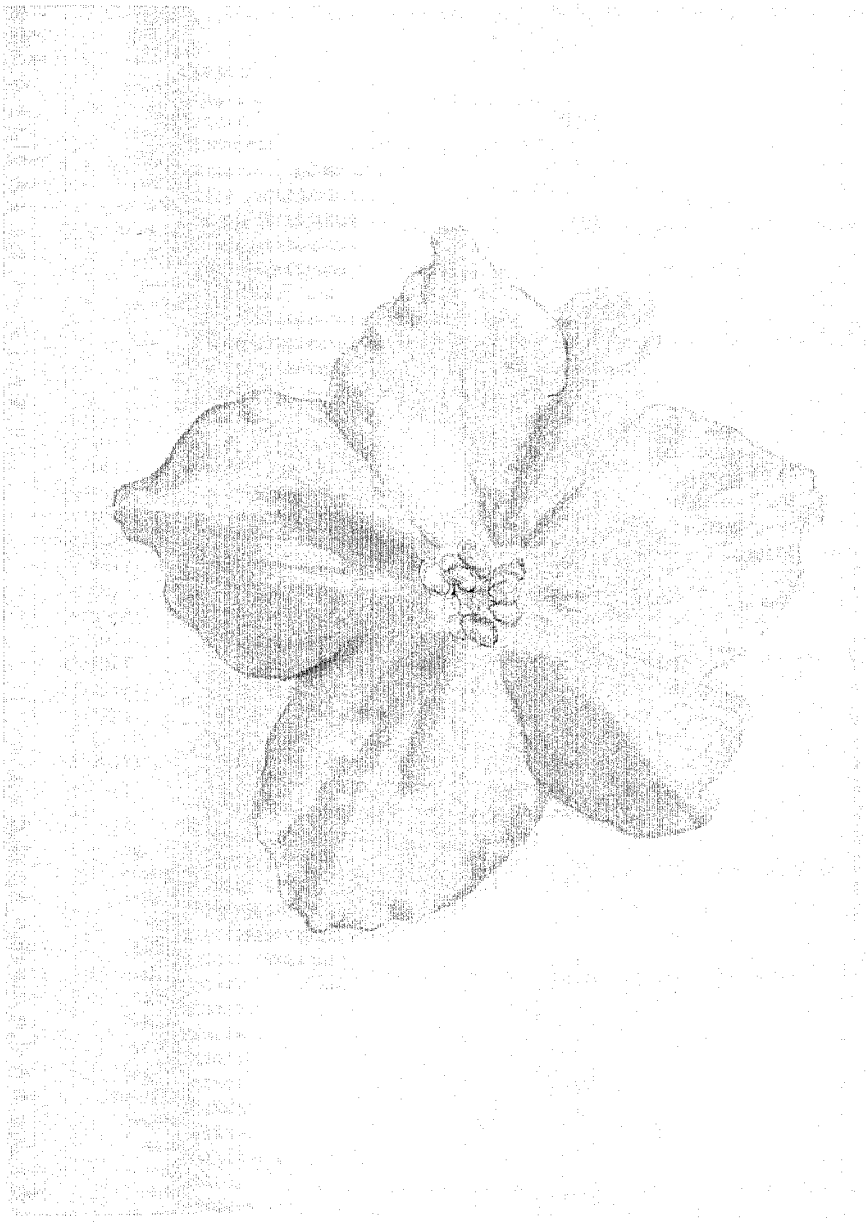

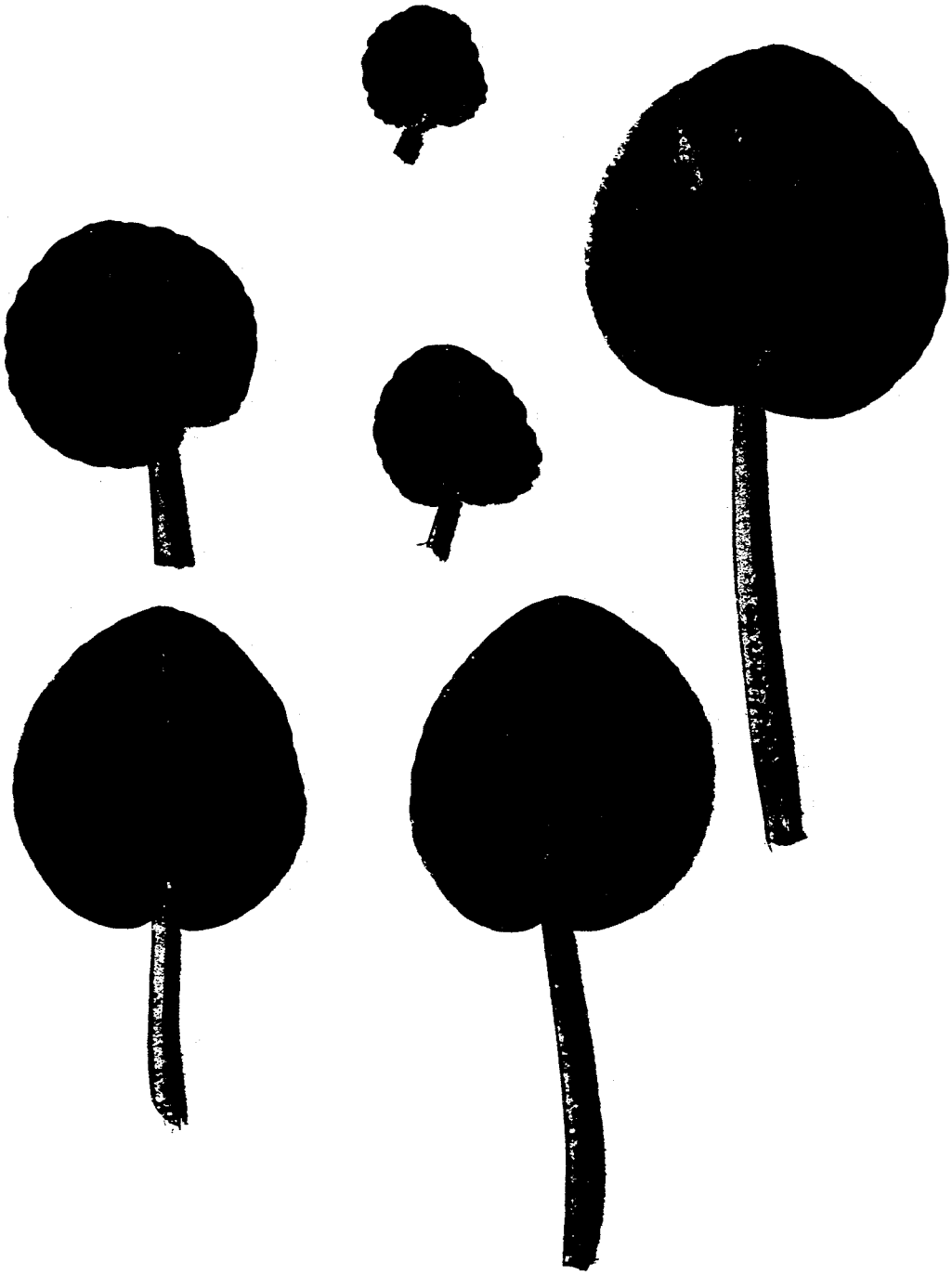

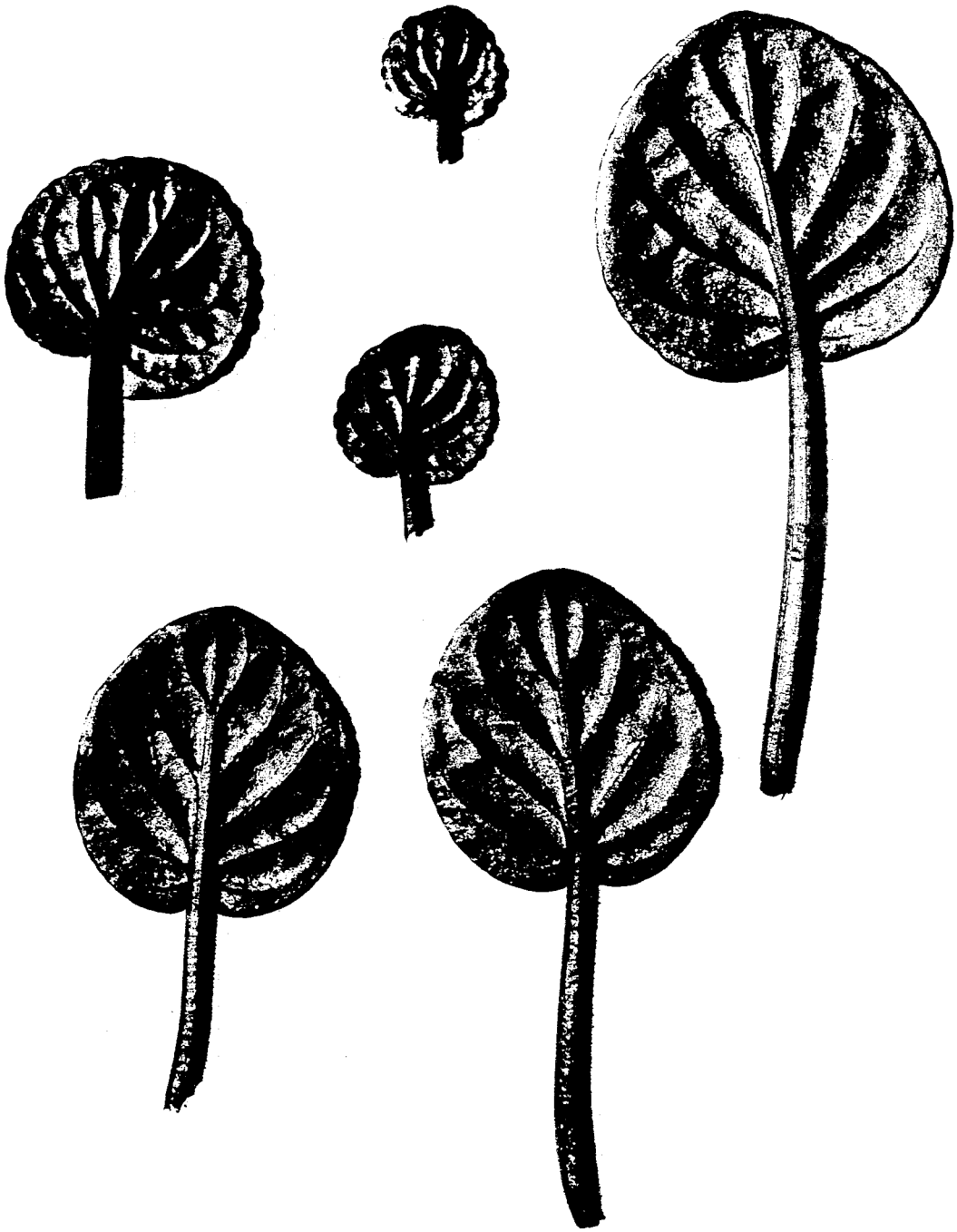

* * * * *